United States Patent
Shibata et al.

(10) Patent No.: US 7,499,162 B2
(45) Date of Patent: *Mar. 3, 2009

(54) METHOD AND APPARATUS FOR OBSERVING AND INSPECTING DEFECTS

(75) Inventors: Yukihiro Shibata, Kanagawa-ken (JP); Shunji Maeda, Kanagawa-ken (JP); Kazuo Yamaguchi, Kanagawa-ken (JP); Minoru Yoshida, Kanagawa-ken (JP); Atsushi Yoshida, Kanagawa-ken (JP); Kenji Oka, Kanagawa-ken (JP); Kenji Watanabe, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/475,667

(22) Filed: Jun. 26, 2006

(65) Prior Publication Data

US 2006/0238760 A1    Oct. 26, 2006

Related U.S. Application Data

(63) Continuation of application No. 10/761,493, filed on Jan. 20, 2004, now Pat. No. 7,092,095, which is a continuation of application No. 09/397,334, filed on Sep. 14, 1999, now Pat. No. 6,690,469.

(30) Foreign Application Priority Data

Sep. 18, 1998    (JP)    ............................... 10-264276

(51) Int. Cl.
    *G01J 4/00*    (2006.01)

(52) U.S. Cl. ...................................................... 356/369
(58) Field of Classification Search .................. None
    See application file for complete search history.

(56) References Cited

U.S. PATENT DOCUMENTS

| 5,333,052 | A | * | 7/1994 | Finarov ....................... 356/369 |
| 5,479,252 | A | * | 12/1995 | Worster et al. ........... 356/237.5 |
| 5,617,246 | A | * | 4/1997 | Hiiro .......................... 359/494 |
| 6,177,984 | B1 | * | 1/2001 | Jacques ....................... 356/39 |
| 6,690,469 | B1 | * | 2/2004 | Shibata et al. .............. 356/369 |

* cited by examiner

*Primary Examiner*—Tarifur Chowdhury
*Assistant Examiner*—Tara S Pajoohi
(74) *Attorney, Agent, or Firm*—Townsend and Townsend and Crew LLP

(57) ABSTRACT

A defect inspecting apparatus includes a sample mounting device for mounting a sample; lighting and detecting apparatus for illuminating a patterned sample mounted on a mount and detecting the optical image of the reflected light obtained therefrom. Also included is a display for displaying the optical image detected by this lighting and detecting apparatus; an optical parameter setting device for setting and displaying optical parameters for the lighting and detecting apparatus on the display; and optical parameter adjusting apparatus for adjusting optical parameters set for the lighting and detecting apparatus according to the optical parameters set by the optical parameter setting apparatus; a storage device for storing comparative image data; and a defect detecting device for detecting defects from patterns formed on the sample by comparing the optical image detected by the optical image detecting apparatus with the comparative image data stored in the storage.

8 Claims, 11 Drawing Sheets

FIG. 6
RECIPE SCREEN

- WAFER ID:
- WAFER TYPE:
- INSPECTION AREA:
- INSPECTION METHOD:
- IMAGE PROCESSING PARAMETER:
- OPTICAL PARAMETER:

915

OPTICAL PARAMETER SETTING SCREEN 916

1. POLARIZING CHARACTERISTICS
POLARIZING CHARACTERISTICS NO.:
→WHEN NOT SET YET, ENTER THE FOLLOWING CHOICES.

| PATTERN TYPE | | | | |
|---|---|---|---|---|
| ORIENTATION FLAT SIDE | ORIENTATION FLAT SIDE | ORIENTATION FLAT SIDE | ORIENTATION FLAT SIDE | ORIENTATION FLAT SIDE |

2. WAVELENGTH
WAVELENGTH SELECTING FILTER NO.:
→WHEN NOT SET YET, ENTER THE FOLLOWING DATA.
THICKNESS OF INSULATING FILM:   $\mu$m
SPECTRUM REFLECTION FACTOR (FILE NAME):

3. LIGHTING $\sigma$
APERTURE DIAPHRAGM NO.:
→WHEN NOT SET YET, SELECT ONE OF THE FOLLOWING CHOICES.

| PATTERN TYPE | |
|---|---|

4. SPACE FILTER
SPACE FILTER NO.:

FIG. 9

| VIBRATING DIRECTION OF POLARIZED LIGHT | | DIFRACTED LIGHT IMAGE | PATTERN IMAGE | CONTRAST | SUM OF SECONDARY DIFFERENTIAL VALUES |
|---|---|---|---|---|---|
| LIGHTING | DETECTING | | | | |
| θ:90° | θ:45° | | | 0.25 | 198205 |
| θ:68° | θ:45° | | | 0.24 | 205331 |
| θ:0° | θ:45° | | | 0.03 | 65331 |
| ⋮ | | | | | |

LIGHT INTENSITY DISTRIBUTION AT A-A

LIGHT INTENSITY DISTRIBUTION AT A-A

METHOD AND APPARATUS FOR OBSERVING AND INSPECTING DEFECTS

BACKGROUND OF THE INVENTION

This invention relates to a high resolution optical system used for inspecting and observing fine pattern defects, foreign matter, etc, which appear, for example, in manufacturing processes of semiconductor devices and flat panel displays. The invention also relates to a defect inspecting apparatus that uses such a high resolution optical system.

A conventional technique, which has provided a method and an apparatus for photographing the structures of fine lines in width using an optical microscope, is disclosed in Japanese Patent Laid-Open No. 7-128595. This technique is characterized by the use of light which is linearly polarized by a polarizer positioned at about 45° to the linear dimension of a sample. The optical delay axis of a ¼ wavelength plate placed between the polarizer and the sample is angled optimally (25° typically) to the main linear shape of the sample. This ¼ wavelength plate converts the linearly polarized light to elliptically polarized light, which is then applied to the sample. This elliptically polarized light, when reflected from the sample, has a phase difference. The reflected light passes through the ¼ wavelength plate again, then passes through a polarizer provided in a detecting light path. The light passing through the polarizer forms an image of the sample on a photoelectric conversion element. In such conventional apparatus, therefore, the phase difference caused by the sample is estimated beforehand, enabling the light set as elliptic polarized light to be converted to circularly polarized light after reflection from the sample.

In the method and apparatus for imaging structures of fine line width using an optical microscope as described, a polarizer is disposed in a lighting light path, and a linearly polarized light is passed through the polarizer. Then this linearly polarized light is converted to an elliptic polarized light through the ¼ wavelength plate before it is applied to the sample. In such an optical system, therefore, both 0-order diffracted light reflected from the sample and higher-order diffracted light become circularly polarized light, and the ratio between the amplitudes of the 0-order diffracted light effective for forming optical images and higher-order diffracted light is the same as that of the random polarized light (the amplitude of the 0-order diffracted light is larger than that of the higher-order diffracted light). Consequently, the 0-order diffracted light and the higher-order diffracted light interfere with each other, thereby degrading the resolution of the optical image of the sample, particularly because the amplitude of the higher-order diffracted light is small, and this causes the low frequency component to be increased.

If an image sensor is used for detecting images, the light intensity is adjusted so as to prevent saturation. For example, because a cyclical fine pattern increases the diffraction angle, the contrast between patterns is small, making detected images dark. If a pattern image is detected and this detected image is processed for defect inspection, the small difference in contrast between patterns, and the dark image causes lower detection sensitivity.

SUMMARY OF THE INVENTION

The present invention provides an optical system that can control the polarization of both 0-order diffracted light used to form optical images and higher-order diffracted light, thereby detecting object patterns for inspection at a high resolution, enabling detection of finer defects.

To achieve this, the invention provides a method for observing a sample with patterns formed thereon. The method includes applying a polarized light to the sample through an objective lens, detecting the polarized light applied to and reflected from the surface of the sample through the objective lens, thereby calculating a deviation of the polarized light from the focal point on the surface of the sample in the axial direction thereof, then adjusting the height of the sample to the objective lens according to the calculated deviation from the focal point, and detecting the polarized light reflected from the surface of the height-adjusted sample through the objective lens, as well as a phase difference plate and an analyzer.

The present invention also provides another method for observing a sample with patterns formed thereon using an optical system. The method includes the steps of applying a polarized light to the sample from the optical system set on a first polarizing condition, detecting the light applied to and reflected from the surface of the sample through a phase difference plate and an analyzer to thereby obtain a first image, displaying the first image on a monitor screen, setting the optical system on a second polarizing condition according to the displayed first image, applying the polarized light to the sample while the optical system is set on the second polarizing condition, and detecting the light applied to and reflected from the surface of the sample through the phase difference plate and the analyzer, thereby obtaining the second image.

The present invention also provides an apparatus for observing a sample with patterns formed thereon. The apparatus comprises a light source for applying a polarized light to the sample through an objective lens, a focal point detector for detecting the light applied to and reflected from the surface of the sample through the objective lens, and calculating a deviation of the polarized light from the focal point on the surface of the sample in the axial direction thereof, a height adjustment device for adjusting the height of the sample to the objective lens according to the deviation from the focal point, calculated by the focal point detecting means, and a polarized light detector for detecting the light reflected from the surface of the sample through the objective lens, as well as a phase difference plate and an analyzer when the polarized light is applied from the lighting means to the sample whose height is adjusted by the height adjusting means.

In another embodiment, the present invention provides a method for inspecting defects of a sample with patterns formed thereon. The method includes the steps of applying a polarized light to the sample through an objective lens, detecting the polarized light applied to and reflected from the surface of the sample through the objective lens, as well as a phase difference plate and an analyzer, thereby obtaining an image of the surface of the sample, then comparing the obtained image with a corresponding image stored beforehand, thereby detecting defects of the sample.

In yet another embodiment, the present invention also provides a method for inspecting defects of a sample with patterns formed thereon which method includes the steps of applying polarized light to the sample from an optical system set on a first polarizing condition, detecting the light applied from the optical system and reflected from the surface of the sample through a phase difference plate and an analyzer to thereby obtain a first image, displaying the first image on a monitor screen, setting the optical system on a second polarizing condition according to the first image displayed on the monitor screen, applying polarized light to the sample while the optical system is set on the second polarizing condition, detecting the light applied to and reflected from the surface of the sample through the phase difference plate and the analyzer to thereby obtain a second image, then comparing the second image with a corresponding image stored earlier so as to detect defects of the sample.

Further, the present invention also provides apparatus for inspecting defects of a sample with patterns formed thereon, the apparatus comprising a light for applying a polarized light to the sample through an objective lens, a polarized light image detector for detecting the light reflected from the surface of the sample through the objective lens, as well as a phase difference plate and an analyzer when the polarized light is applied to the sample to thereby obtain an image of the sample, and a defect detector for comparing the image obtained by the polarized light image detector with a corresponding image stored beforehand so as to detect defects of the sample.

Further, the present invention also provides a high resolution optical system comprising an optical system for applying a polarized light to a sample, an optical part for polarization for passing a higher-order diffracted light, which is polarized and rotated by the sample, more efficiently than the 0-order diffracted light, and an optical system for detection, used for forming an image of the sample on a photoelectric conversion element with the light passing or reflected from the optical part for polarization. (For example, the high resolution optical system applies a polarized light to the sample with oscillations orthogonal to a line pattern of the sample and the optical system is provided with a polarizer disposed so as to assume the vibrating direction of 45° to the pattern, as a transmission axis.)

This polarized light can originate from a light passing or reflected from a polarized light beam splitter. If such a light is used, a ½ wavelength plate and a ¼ wavelength plate are disposed between the polarized light beam splitter and the sample, so that the ½ wavelength plate is rotated according to the orientation of the pattern, etc., thereby rotating the polarizing direction, and the ¼ wavelength plate is rotated, thereby adjusting the ellipticity of polarization.

Further, the present invention allows the combination of the 0-order diffracted light used to form optical images and the direction of the higher-order diffracted light to be varied in many ways. The combination is important for making the high resolution optical system practical. The high resolution optical system is provided with functions for collecting images detected respectively by changing the polarization status and carrying out a preliminary defect inspection so as to select a polarizing condition for improving the defect inspect sensitivity. The optimal value for the polarizing condition can thus be found correctly and quickly.

BRIEF DESCRIPTION OF THE DRAWINGS

FIG. 6 illustrates a recipe display and an optical parameter setting display;

FIG. 9 illustrates diffracted light images and pattern images;

DESCRIPTION OF THE SPECIFIC EMBODIMENTS

Figure 1A:
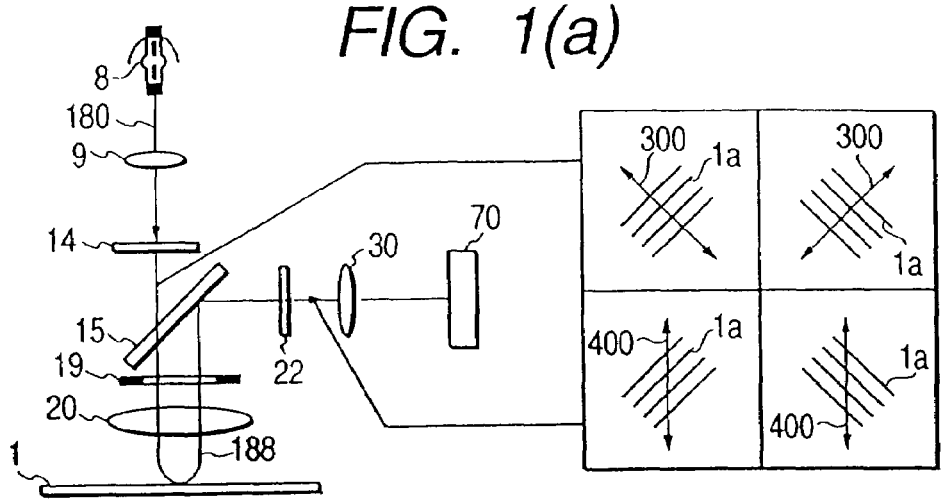
FIG. 1(a) is a schematic front cross-sectional view of an embodiment of a high resolution optical system of the present invention.

An embodiment of the high resolution optical system of the present invention will be described with reference to FIG. 1(a). A light 180 emitted from a light source 8 is condensed by a lens 9 and passed through a polarizer 14. The light 180 thus becomes linearly polarized light and passes through a half-mirror 15. After passing through half-mirror 15, the light 180 strikes a sample 1 through an objective lens 20. Light 180 is reflected form the sample 1 and becomes diffracted light 189. Part of the diffracted light 189 enters the NA (Numerical Aperture) of the objective lens 20, then reflected from the half-mirror 15 to an image sensor 70. Detected light 189, when oscillating in the direction of the electric field vector (hereafter, the polarized direction of the light) on the polarizing plane corresponding to the transmission axis of the polarizer 22, where it forms an image of the sample 1 on the image sensor 70 through image-forming lens 30.

The polarizer 14 determines the direction in which the polarized light vibrates with respect to the direction 1a of the main pattern formed on the sample 1. (The main pattern is often the result of an upper layer of conductive material patterned into fine metal lines.) Therefore, the polarizer 14 is positioned so as to polarize light in an orthogonal direction to the direction 1a of the pattern to detect. This plane of the polarized light is in the direction at the injection eye 19 of the objective lens 20. The polarizer 22 passes part of the detected light 189, to be transmitted in a specific vibrating plane to the pattern orientation 1. For example, polarizer 22 is set to an angle of 45°.

Figure 1B:
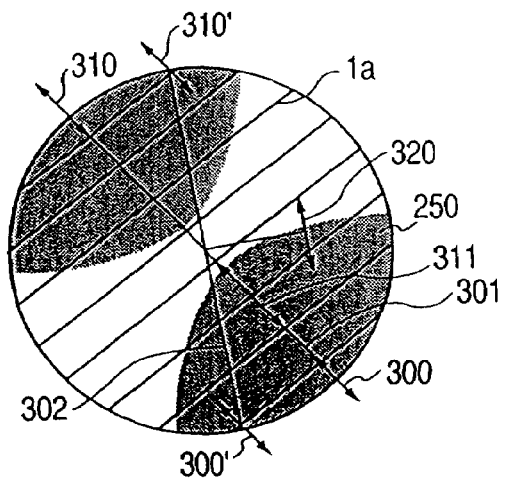
FIG. 1(b) illustrates light on an object lens and diffracted light reflected from a sample.
Figure 1C:
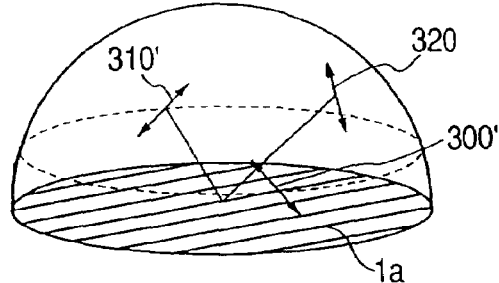
FIG. 1(c) shows polarization of the illumination source and polarization of diffracted light reflected from the sample.
Figure 1D:
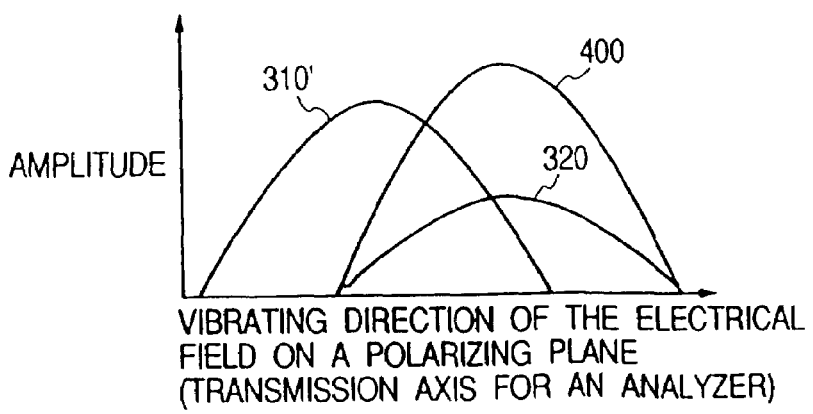

Next, we describe the light source, as well as the polarization of the 0-order diffracted light and higher-order diffracted light reflected from the sample 1 with reference to FIG. 1(b). We also describe the polarization of the light applied to the sample 1, as well as the polarization of the 0-order diffracted light and the higher-order diffracted light reflected from the sample 1, all with reference to FIG. 1(*c*).

In FIG. 1(*b*) it is assumed that the light polarized at one point of the illumination light 180 on the injection lens is polarized as shown by 300. This polarized light 300 matches, or is orthogonal to, the direction 301 for sample 1. Thus, the polarization 310' of the reflected light (0-order diffracted light) and the polarization 311 of the higher-order diffracted light are the same as the polarization of the illumination source. The linear polarization is converted to elliptical polarization, because a phase difference is created when the light is reflected and diffracted from sample 1.

If the polarization direction 300' of the light 180 does not match, nor is orthogonal to, the direction for illumination of sample 1, the polarization direction 310' of the 0-order diffracted light matches with the polarization direction 300' of the illumination source. The polarization direction 320 of the higher-order diffracted light differs from the polarization direction 300' of the illumination source due to rotation of polarization. (The actual polarization direction is distributed and the polarization direction mentioned here is the direction of the largest amplitude.) Consequently, as shown in FIG. 1(*d*), the polarization direction 310' of the 0-order diffracted light differs from the polarization direction 320 of the higher-order diffracted light. It is thus possible to increase the amplitude of the higher-order diffracted light on the image surface by matching the transmission axis of the polarizer 22 with the polarization direction 320 of the higher-order diffracted light. Consequently, the 0-order diffracted light and the higher-order diffracted light become almost equal in amplitude and the resolution of the optical image formed due to the interference between the 0-order diffracted light and the higher-order diffracted light is improved.

Figure 2:
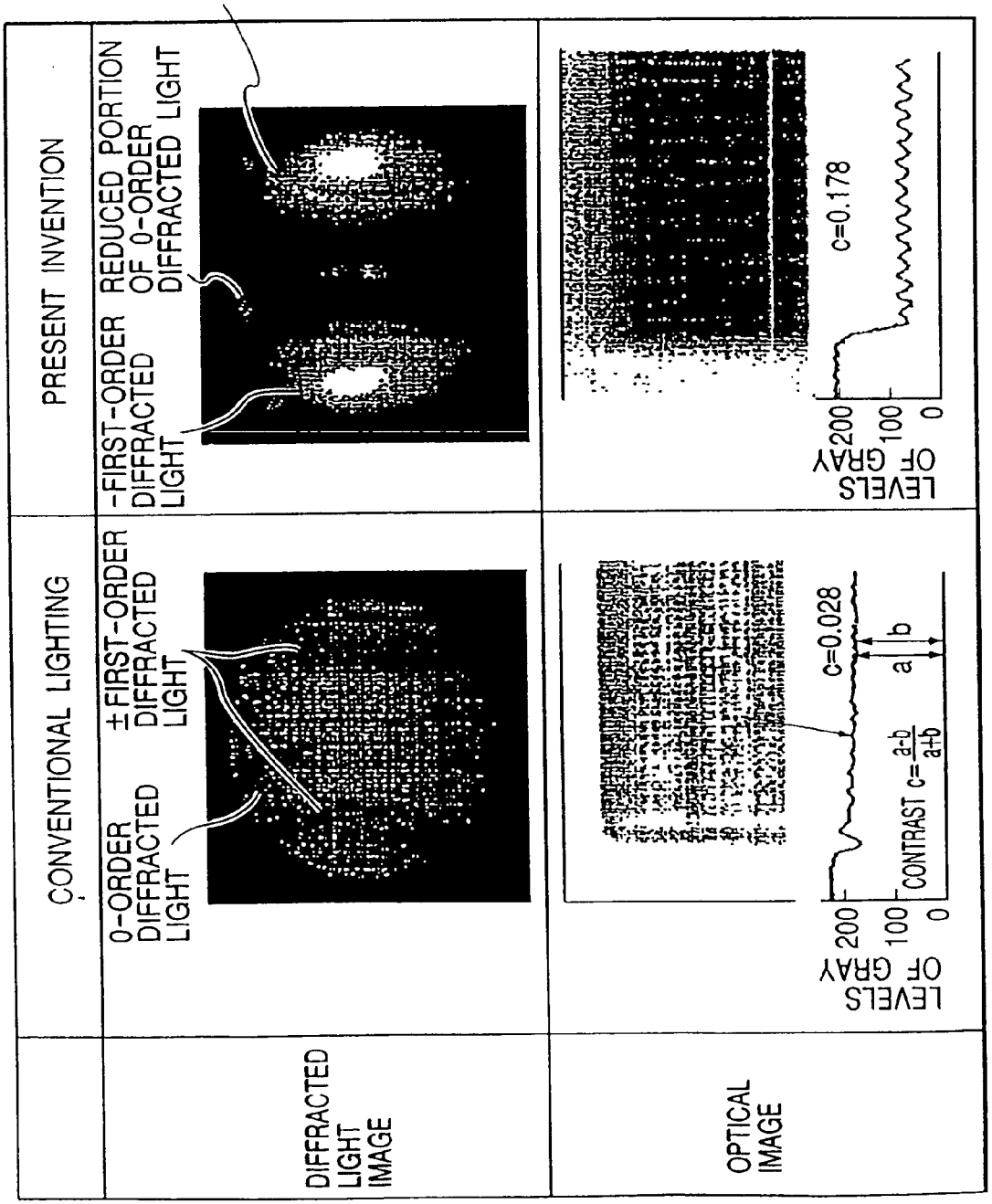
FIG. 2 illustrates detection results of optical images of patterns detected by the conventional down-lighting and by an embodiment of the present invention.

FIG. 2 shows diffracted light images and optical images of a pattern of lines and spaces when defects are detected using a conventional down lighting method and using a polarized light method of the present invention, respectively. The transmission axes of the polarizers 14 and 22 used for obtaining images using the polarized light method of the present invention are the same as those shown in FIG. 1.

Numeral value 1 is set for σ in both the conventional down lighting method and the polarized lighting method of the present invention. The diffracted light image obtained by the conventional down lighting method distributes the 0-order diffracted light. The approximately first-order diffracted light is darker, and has less amplitude than the 0-order diffracted light.

In contrast, if the polarized lighting method of the present invention is used, the diffracted light image obtained will be greater than the first-order diffracted light in amplitude, and detected as a brighter image. The approximately first-order diffraction image also includes the 0-order diffracted light. More precisely, the first-order diffraction image is the sum of the 0-order diffracted light corresponding to the positive first-order diffracted light and the negative first-order diffracted light distribution. This is also true for the positive 1-order diffracted light image. And, the reduced portion of the 0-order diffracted light is not detected in the diffracted light image at the injection point 19 of the objective lens 20, because the corresponding higher-order diffracted light is outside the NA of the objective lens 20. (The diffraction angle of this first-order diffracted light is determined by both wavelength and pattern width.)

Accordingly, the light at the reduced portion of the 0-order light is a low frequency component not used to form the image of the sample 1. Thus, the image resolution can be improved due to such reduction. With the conventional down-lighting method it is difficult to separate lines and spaces from each other, because the contrast of the lines and spaces (found from the peak (a) and the bottom (b) of the detected contrast difference signal) is low (C=0.028). The method of the present invention, however, can separate lines and spaces from each other clearly, because in one embodiment the contrast is improved to 0.178. According to the present invention, it will be understood that the resolution is improved significantly compared to the conventional method.

Figure 3:
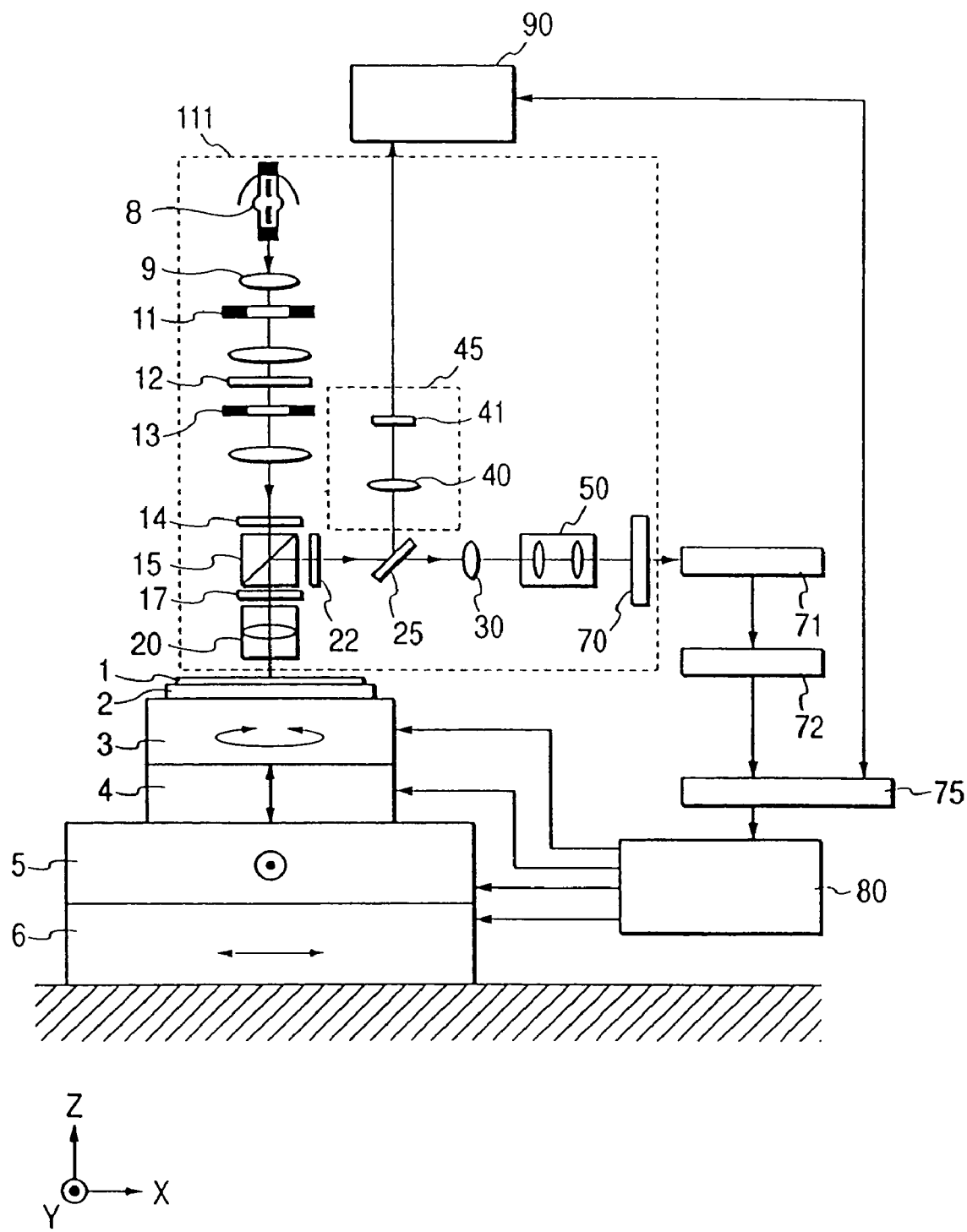
FIG. 3 is a schematic front cross-sectional view of a defect inspection apparatus in a first embodiment of the present invention.

FIG. 3 illustrates a first embodiment of a defect inspecting apparatus that uses the optical system of the present invention. A sample 1, for example, a wafer, is held by a vacuum chuck 2. Chuck 2 is mounted on a θ-stage 3 so as to be above a Z-stage 4, a Y-stage 5, and an X-stage 6, respectively. An optical system 111 disposed above the sample 1 is used to detect the optical image of the sample 1, enabling inspection of the external appearance of each pattern formed on sample 1. The optical system 111 mainly comprises a lighting system, a detection optical system for photographing the image of the sample 1, and a focal point detection optical system 45.

A light source 8 in the lighting optical system is an incoherent light source, for example, a xenon lamp. The light emitted from light source 8 is transmitted through the aperture of a diaphragm 11 and through a lens 9. The light, which passes through a wavelength selecting filter 12 and another lens, reaches a visual field diaphragm 13. This wavelength selecting filter 12 limits the wavelength range, thereby detecting a high resolution image of the sample 1 by taking the spectral reflection factor of the sample 1 into consideration. For example, an interference filter is employed. The light, which passes through the visual field diaphragm 13, passes through a polarizer 14 to become a linearly polarized light. This polarized light then passes through a half-mirror 15 and enters an objective lens 20 to illuminate sample 1.

After illuminating the sample 1, the light is reflected, scattered, and diffracted by the sample, and part of the light enters the objective lens 20 again and reaches the half-mirror 15. The light is then reflected from the half-mirror 15 and enters the polarizer 22. The polarizer 22 is positioned around the reflected light axis so as to transmit the higher-order diffracted light more than the 0-order diffracted light. Passing through the polarizer 22, the light passes through the image forming lens 30 and the zoom lens 50, then forms an image on the light-receiving surface of the image sensor 70. The image sensor 70 is, for example, a linear sensor, a TDI image sensor, a TV camera, or other imaging device.

At this time, the focal point detection light must be provided to the focal point detecting optical system 45 for automatic focusing of the object image. The light dividing means 25, for example, can be a dichroic mirror. The focal point detection light forms an optical image having the height information of the sample 1 on the sensor 41 through the image forming lens 40. The output signal from the sensor, which detects this optical image, is supplied to a focal point detection signal processing circuit 90. Circuit 90 detects the deviation between the height of the sample 1 and the focal point of the objective lens 20, thus transmitting the detected deviation to the CPU 75. Using this deviation value, the CPU 75 instructs the stage controller 80 to drive the Z-stage 4 so the stage controller 80 transmits a predetermined pulse to the Z-stage 4. The automatic focusing function is thus stated.

The image signal obtained by detecting the optical image of the sample 1 at a photoelectric conversion element 70 is provided to an image processing circuit 71 so as to store the image and determine defects. The X-stage 6 and the Y-stage 5 are used for moving the sample in two dimensions in the X-Y directions. The θ-stage 3 is used for rotational alignment of the pattern formed by the sample 1.

Although the optical system of the down-lighting method has been described in this embodiment, the resolution R of this optical system is generally found from an expression of $R=\lambda/(2NA)$. As shown in FIG. 2, however, an optical system that uses linearly polarized light can obtain a higher resolution than R.

Next, second embodiment of the defect inspecting apparatus of the present invention will be described with reference to FIG. 4. The light emitted from a light source 8 passes through an aperture diaphragm 11 via a lens 9 and enters a polarized light beam splitter 15 via a wavelength selection filter 12 and a visual field diaphragm 13. The light, which passes a λ/2 plate (½ wavelength plate) 16 and a λ/4 plate (¼ wavelength plate), illuminates the sample 1 through an objective lens 20. The λ/2 and λ/4 plates provide a phase difference to the P-polarized light passing through the polarized light beam splitter 15. By rotating the λ/2 plate 16 around the light axis, the polarizing direction of the polarized light is set at a predetermined angle (e.g., 90° shown in FIG. 1). The λ/4 plate 17 is a phase difference plate for transforming the linearly polarized light to elliptically polarized light. The detected light, which illuminates sample 1 through the objective lens 20, passes through the λ/2 and λ/4 plates 16 and 17 again and is reflected by beam splitter 15, and it is led into the detected light path.

Figure 4:
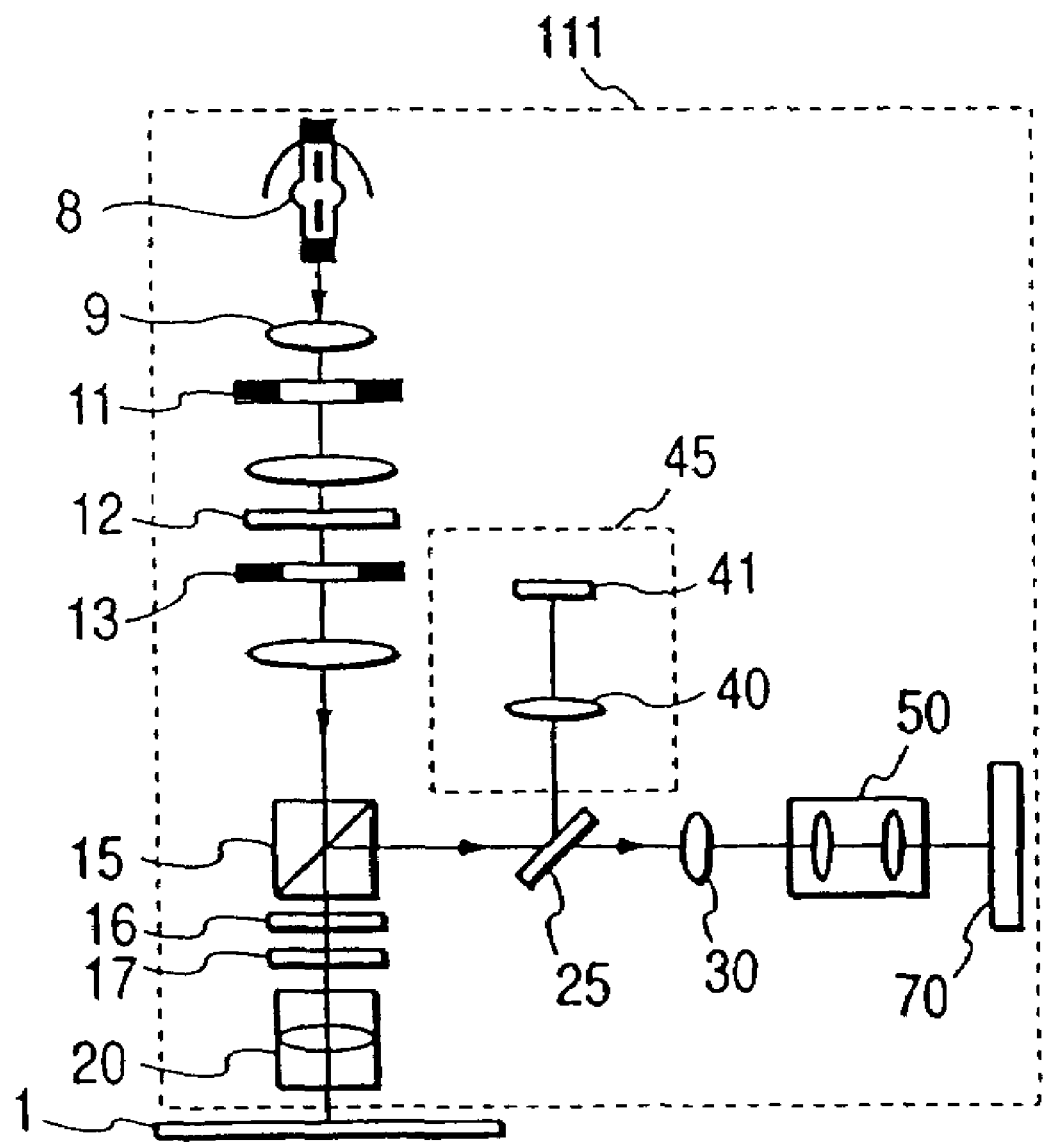
FIG. 4 is a schematic front cross-sectional view of a defect inspection apparatus in a second embodiment of the present invention.

If no λ/4 plate 17 is used in the optical configuration shown in FIG. 4, the light reflected positively (0-order diffracted light) by the sample 1 passes through the polarized light beam splitter 15. Therefore, only the higher-order diffracted light is provided to the detecting light path. If a polarized light beam splitter 15 is used and provided with the same functions as those of the polarizers 14 and 22 in the configuration shown in FIG. 3, a λ/4 plate 17 provides 0-order diffracted light having the same amplitude as the higher-order diffracted light to the detecting light path.

If 45° is taken between the light axis of the crystal of the λ/4 plate 17 and the polarizing direction of the illumination, the light passing through the λ/4 plate 17 becomes circularly polarized light. In this case, the light intensity supplied to the detecting light path is increased. This is because the light intensity of the 0-order diffracted light, which is a low frequency component, is increased. As a result, the contrast of the image is lowered more than the linearly polarized light. This is why the optimized angle between the light axis of the crystal of the λ/4 plate 17 and the polarization direction of the illumination source is changed by, for example, the phase difference of the sample 1. Accordingly, the λ/4 plate 17 should be allowed to rotate to enable the phase difference of the sample 1 to be changed. If the plate 17 is so composed, part of the light reflected and diffracted by the sample 1 passes through the λ/2 and λ/4 plates 16 and 17 again and is reflected by the polarized light beam splitter 15, thereby forming an optical image of the sample 1 on the image sensor 70.

Figure 5A:
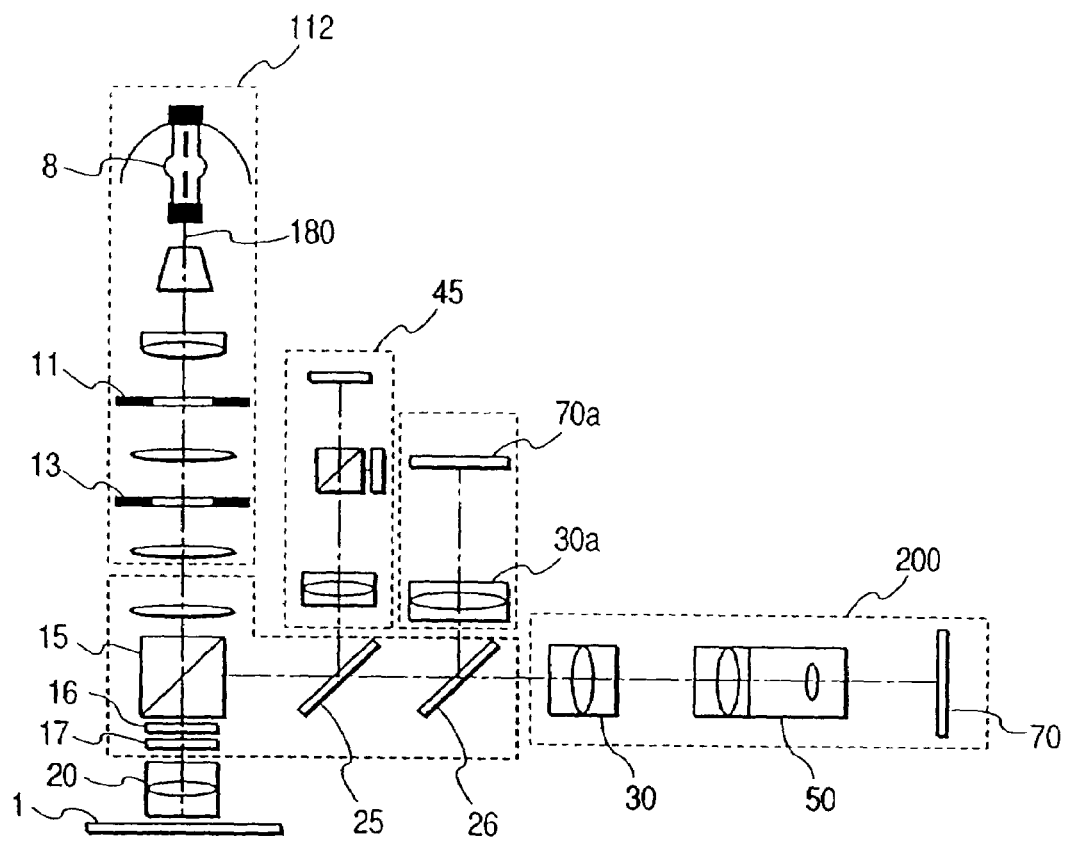
FIG. 5(a) is a schematic front section view of a defect inspection apparatus in a third embodiment of the present invention.
Figure 5B:
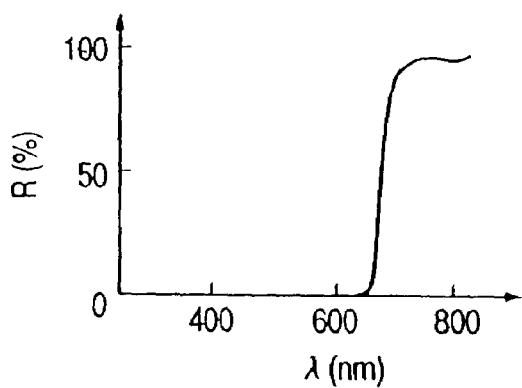
FIG. 5(b) shows the wavelength range for detecting a focal point.
Figure 5C:
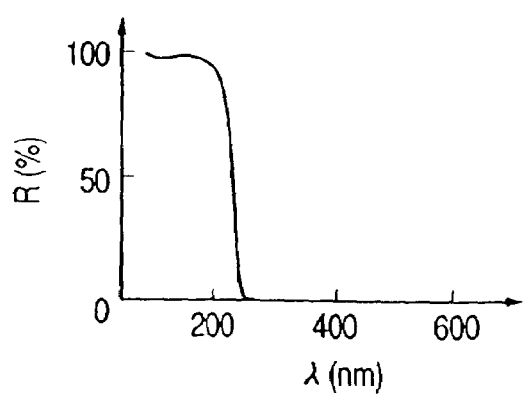
FIG. 5(c) shows a spectrum reflection factor of the second dichroic mirror.

The third embodiment of the defect inspecting apparatus of the present invention is described with reference to FIG. 5. In this embodiment an illumination source of less than 200 to 250 nm in wavelength is employed. Because resolution is improved with a shorter wavelength, the use of an ultra-violet light or a DUV (Deep Ultra Violet) light is effective to further improve resolution. The optical system shown in FIG. 5(*a*) allows a light emitted from an ultra-violet beam source 8 to pass to a beam splitter 15 through optical system 112. The polarized light passing through this beam splitter 15 passes the λ/2 and λ/4 plates 16 and 17, so that the light has a phase difference. The light then strikes sample 1 from above through the objective leans 20. The down-lighting consists of an ultra-violet light for the visual field and a focal point light for detecting the height of the sample 1.

The focal point light is effective if it is visible light, which is not absorbed by a flattening film. If light is completely absorbed by a flattening film, the height of the sample 1 cannot be detected. The wavelength for this focal point detecting light is determined by the spectrum reflection factor of the dichroic mirror 25. FIG. 5(*b*) shows an example in which light of not less than 650 nm in wavelength is used as such a focal point detecting light.

The light path for detecting bright-field images using an ultra-violet light is a light path reflected from the second dichroic mirror 26. The light path detects images on the surface of a sensor 70*a* through an image forming lens 30*a*. This ultra-violet beam wave range is determined by the spectrum reflection factor of the second dichroic mirror as shown in FIG. 5(*c*).

If the ultra-violet beam is applied to the sample 1, the sample 1 generates a fluorescent light depending on the material. This fluorescent light can be used to detect defect images. In this case, the fluorescent light makes it possible to detect even the defects that cannot be detected in bright-field images. Such an optical system can be put into practical use if it is composed so as to form an intermediate image through an image forming lens from a light passing two dichroic mirrors and project this image expanded by a zoom lens 50 on the image sensor 70. An objective lens for ultra-violet lights can correct the aberration with the ultra-violet beam, but the focal point detecting light should be a light with less aberration from the ultra-violet bean.

FIG. 6 illustrates how to set optical parameters for inspecting defects of a pattern using the defect inspecting apparatus of the present invention, for example, as used in a semiconductor manufacturing process. At first, an inspection recipe is displayed on the screen. The ID of a wafer to be inspected according to this displayed recipe is registered. After that, the type of wafer is entered. This makes it possible to identify the type of each defect, as well as the process in which the defect is detected. Furthermore, the inspection area is specified with, for example, coordinates of the object wafer. Although this defect inspection method detects each defect by obtaining the image of a pattern formed on the object wafer, there are also other inspection methods, including a method for detecting defects by detecting differences by comparison between images of adjacent chips, and a method for detecting differences as a result of comparison between design data and an object image. One of these methods is selected for "Inspection Method." Then, the threshold of a difference image, is entered so as to position image and decide the defect detection sensitivity for "Image Processing Parameters." The defect detection sensitivity is also set so as to change the "Optical Parameters."

Changing the "Optical Parameters" is next described. The menu "Optical Parameters" is selected on the recipe screen to display the "Optical Parameters" setting screen. On this "Optical Parameters" setting screen, necessary parameters are set by selecting from 1, Polarization Characteristics; 2, Wavelength; 3, Lighting σ; and 4, Space Filter, etc. The choice (1, Polarization Characteristics) decides the polarization of both the lighting optical system and the detecting optical system with, for example, a number. If the number for specifying polarization characteristics for higher defect detection sensitivity is already known, the number is entered. However, since such polarization characteristics for higher defect detection sensitivity are not defined yet in the initial inspection of a wafer, polarization characteristics effective for improving the defect detection sensitivity are selected according to the object pattern shape. The relationship between such a pattern shape and polarization characteristics is found, for example, from the relationship shown in FIG. 1(a).

The choice "2, Wavelength" selects a light wave range for a higher contrast for defects. For example, a high wavelength range is selected for a higher reflection factor of the object pattern to inspect. Otherwise, a wavelength range should be selected for a larger difference of brightness between the pattern and the background (no-pattern region). In the case of a wafer treated with chemical mechanical polishing (CMP), if the film thickness is uneven, the brightness of the detected image becomes uneven due to the interference of the insulating film. Since the unevenness of this film thickness is not a defect, the difference of brightness appears as a noise in the defect inspection. To reduce such a brightness difference, increasing the lighting wavelength range is effective. However, because an increase of wavelength range differs between the design thickness of the insulating film and the error, the choice of a lighting wavelength range from the insulating film thickness is effective. This is why the thickness of the object insulating film is entered as a condition for selecting the lighting wavelength range.

The "Lighting σ" selects an aperture diameter of the aperture diaphragm 11 of the lighting system. If a hole-like pattern is formed on the sample 1, the lighting σ value should be set smaller than that of the line-like pattern so as to improve the defect detection sensitivity.

A space filter is an optical filter for reducing the amplitude transmission factor of the 0-order diffracted light or giving a phrase difference to the 0-order diffracted light at a Fourier transformation surface (the injection point of an objective lens or at a position common to this injection point (the position of the zoom lens 50)). Disposition of such a space filter according to the shape, density, etc., of the object pattern enables the resolution of the image to be improved. If the optical parameters are set as described, the image is sensed more effectively for detecting defects. Whether or not the set conditions are proper, however, depends on the shape of the object pattern and the structure of the object wafer.

Figure 7A:
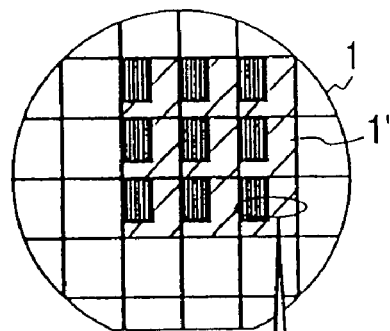
FIG. 7(a) is a top view of a wafer to be inspected.
Figure 7B:
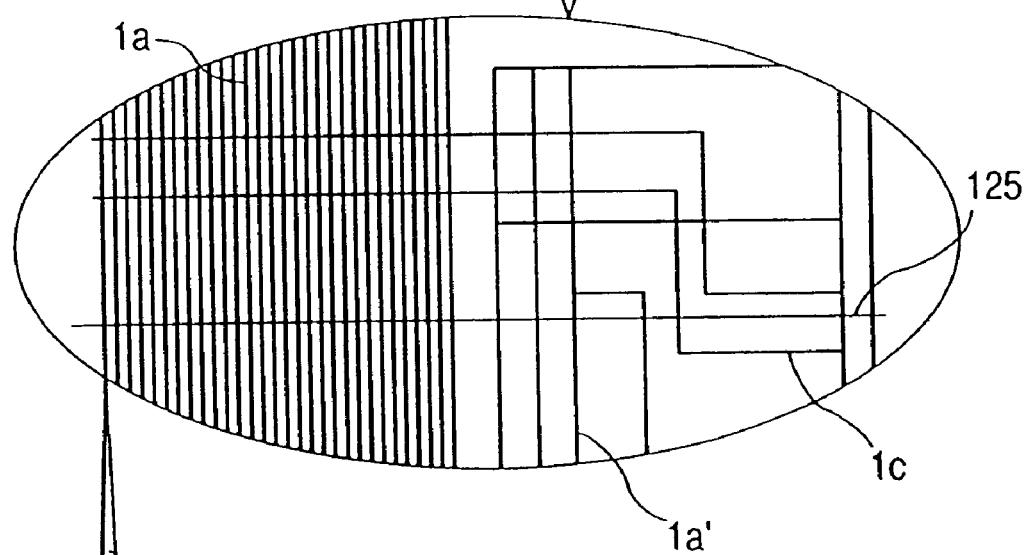
FIG. 7(b) is an expanded top view of part of the wafer shown in FIG. 7(a)
Figure 7C:
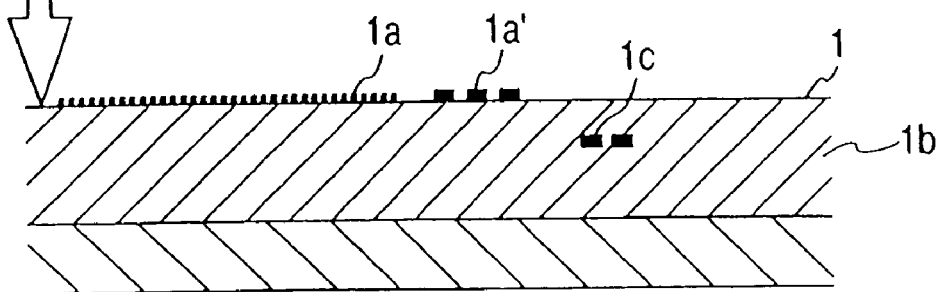
FIG. 7(c) is a cross-sectional view of the wafer, which is cut at line 125.

As shown in FIG. 7(a), patterns are disposed regularly on a wafer in units of an exposure field of the object. FIG. 7(b) shows an expanded view of the 1' portion of the wafer 1. The wafer 1 has patterns 1a and 1a' to be inspected, as well as a pattern 1c, etc., formed on the previous process. FIG. 7(c) shows a cross-sectional view of the wafer 1, which is cut at the line 125. It is assumed that the patterns 1a and 1a' to be inspected are formed on an insulating film 1b, and the pattern 1c, not to be inspected, is formed in the insulating film 1b. In this case, the patterns 1a and 1b are to be inspected mainly in the vertical direction. Thus, if optical parameters are set so as to increase the contrast of the object pattern in this direction, the defect detection sensitivity can be improved. However, since the optimal value of each of those optical parameters depends on the shape and structure of the object pattern, time is required to determine such an optical value.

Figure 8:
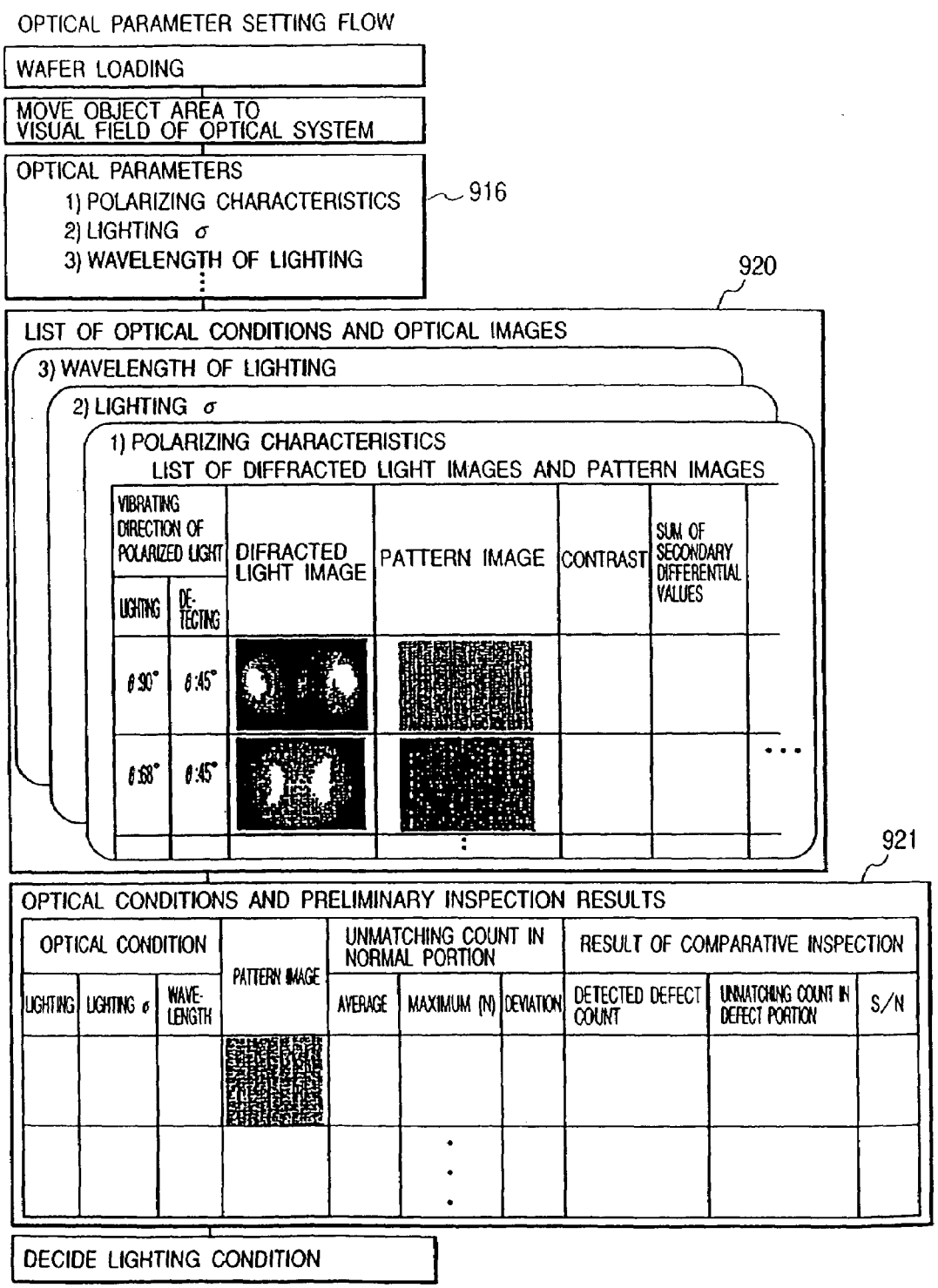
FIG. 8 illustrates a sample flowchart for setting optical parameters.

FIG. 8 is an optical parameter setting flowchart for setting optical parameters quickly and effectively. At first, a wafer is loaded in the inspecting apparatus, then the inspection area is moved into the visual field of the optical system. After that, a necessary parameter range for obtaining a preliminary image is entered for each of the optical parameters (1, Polarization Characteristics; 2, Wavelength; 3, Lighting σ; and 4, Space Filter). Next, each image is obtained using the set conditions and displayed so as to easily check diffracted images and pattern images. In addition, the total sum of secondary differential values indicating pattern contrast and pattern sharpness, etc., are displayed. Consequently, optical parameters, as well as optical image resolution information can be listed to enable optimal values of optical parameters to be decided easily.

The final optical parameters are decided from a viewpoint of whether or not the object image is effective to detect defects. Consequently, the object optical parameter range is narrowed from the contrast and the sum of secondary differential values mentioned above, and finally the optical parameters are decided by changing those parameters while a preliminary inspection is carried out. As a result of such a preliminary inspection, for example, optical parameters are decided according to the inconsistent values (average, maximum, and deviation) of a difference image in a normal portion and the result of comparative inspection (detected defect count, defect signal level, S/N, which is a ratio between the maximum inconsistency value N in a normal portion and an unmatching count in a defect portion S, and other factors). According to such, the optical parameters setting process, at least one of the necessary optical parameters is set, thereby enabling other optical parameters to be set effectively for a high defect detection sensitivity.

FIG. 9 is an example of displaying diffracted light images/pattern images shown in the list of optical conditions and optical images in the optical parameters setting process flow shown in FIG. 8. As an example of displaying a series of diffracted light images/pattern images, the polarization status is assumed as a parameter. At first, the polarization direction of a polarized light may be defined for the directions of the XY stages and the orientation flat of the wafer. For example, 90° and 45° of the polarization direction of the illuminating light and the detecting light mean angels between the main direction of an object pattern to inspect and the polarization direction of the main light beam.

This display makes it possible to estimate a ratio between the amplitude of a higher-order diffracted light and the amplitude of the 0-order diffracted light from a diffracted light image. In addition, if there are many patterns to inspect in various directions, it is possible to detect each of those pattern directions, the contrast, etc., from pattern images. In addition, if the light intensity distribution of an image is displayed with a polygonal line graph, etc., it is easier to recognize the brightness level, etc. In addition, it will be understood from the contrast and the sum of secondary differential values that the resolution of images is improved at around 90° and 68° of the polarization directions of the illumination light. Consequently, if the next preliminary inspection is carried out on this condition, optical conditions for enabling a high sensitivity inspection can be set quickly.

Figure 10A:
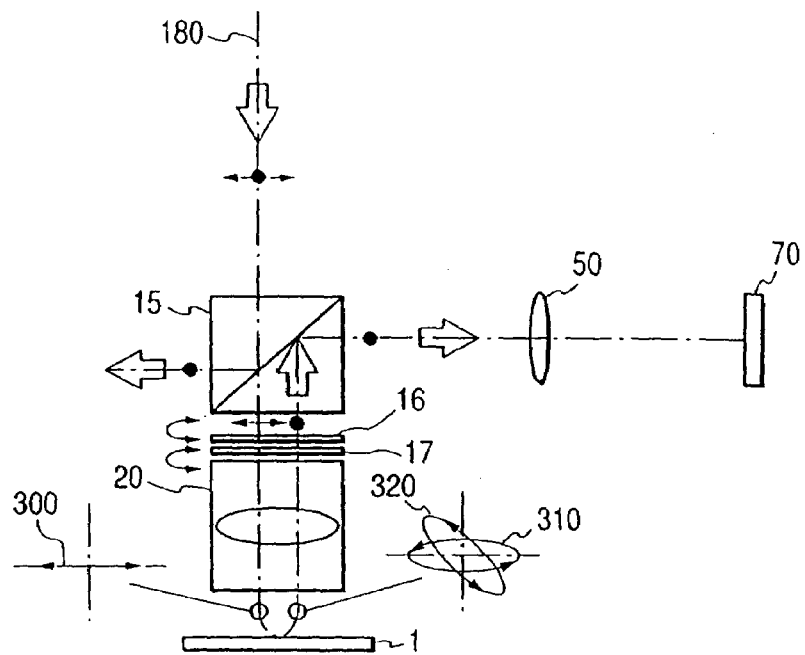
FIG. 10(a) is a schematic cross-sectional view of an embodiment of a lighting/detecting optical system of the present invention, which uses a polarized light.
Figure 10B:
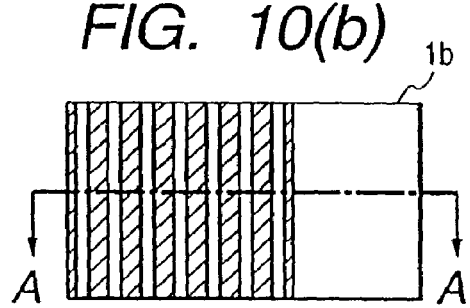
FIG. 10(b) is an image of levels of gray detected in normal bright-field detection.
Figure 10C:
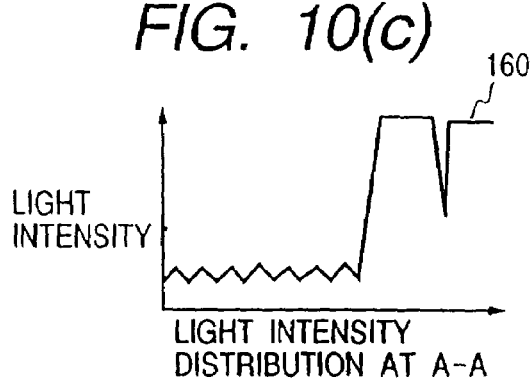
FIG. 10(c) shows the distribution of the brightness at the A-A line in the image of levels of gray.
Figure 10D:
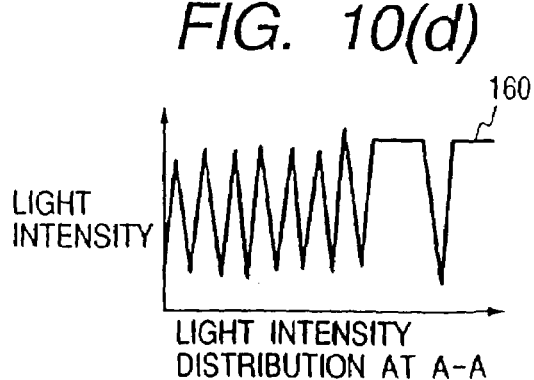
FIG. 10(d) shows the distribution of the brightness at the A-A line of the levels of gray image shown in FIG. 10(b), which is detected by adjusting the phase difference in an embodiment of the present invention.

FIG. 10(a) shows detecting bright-field and dark-field images by polarization, and detecting neutral images of the bright-field and dark-field images. Light 180 is randomly-polarized light. If the light 180 is provided to the polarized light beam splitter 15, only the light having the appropriate polarized light component passes through the splitter 15. This polarized light is then passed through the λ/2 and λ/4 plates 16 and 17, thereby changing both the rotation of the polarization direction and the ellipticity of the polarized light. The illumination, when reflected from the sample 1, is given a phase difference according to the phase jump and the sample pattern, thereby changing the polarization status. If a light is diffracted at an edge of a pattern, etc., the polarization status is also changed according to the direction of the diffracted light. These reflections are caught by the objective lens 20 and passed to the polarized light beam splitter 15 through the λ/2 and λ/4 plates 16 and 17. The polarized light component is reflected from the splitter 15 so as to form a bright-field image on the sensor 70.

If a detected image is a levels-of-gray image as shown in FIG. 10(*b*) in a normal bright-field detection, the brightness distribution at the line A-A will be as shown in FIG. 10(*c*), and the image becomes dark in the dense pattern portion on the left side of the image. Although the contrast of the dense pattern portion can be increased by increasing the light intensity, the brightness in the flat portion on the right side of the image is further increased, saturating the CCD sensor 70 and causing blooming. This is why the light intensity cannot be increased, and the dense pattern cannot be detected without proper contrast. However, if the phase difference is adjusted using the λ/2 and λ/4 plates 16 and 17, it is possible to reduce the light intensity on each flat portion, which is reflected from the polarized light beam splitter as shown in FIG. 10(*d*) and increase the reflection of the diffracted light from the dense pattern portion. The brightness both at a dense pattern and at a flat portion can thus be detected on the same level.

It is therefore possible to detect high contrast images regardless of the pattern density, etc., and detect pattern defects, etc., easily even in a dense pattern portion of the wafer. To achieve this, if linearly polarized light is used to illuminate the sample 1, the polarization direction of the polarized light and the orientation of the pattern are set at right angles. The polarization direction of the polarized light can be rotated by rotating the λ/2 plate.

For a wafer on which a CMP treatment is used, the brightness can become uneven due to the uneven thickness of the film, mainly in areas of lower pattern density. Because this brightness unevenness is not a fatal defect, the noise appearing during defect detection can be reduced by reducing the detected light intensity at a flat portion. Consequently, if the reflected light intensity from a flat portion is set lower than that from a high pattern density portion, it is possible to increase the defect signal of the high pattern density portion whose fatality is comparatively high, and reduce the noise caused by a reflected light from the flat portion whose fatality is comparatively low. As described above, defects can be detected even with CMP wafers at a high sensitivity.

In the optical system as illustrated in FIGS. 3, 4, 5 and 10, linearly polarized light reaches a ¼ wavelength plate 17 and is converted into elliptically polarized light. The elliptically polarized light strikes the sample 1 through the objective lens 20. Light reflected or refracted from the sample is collected by the object lens 20 and its phase is shifted by passing through the ¼ wavelength plate 17 again.

Figure 11:
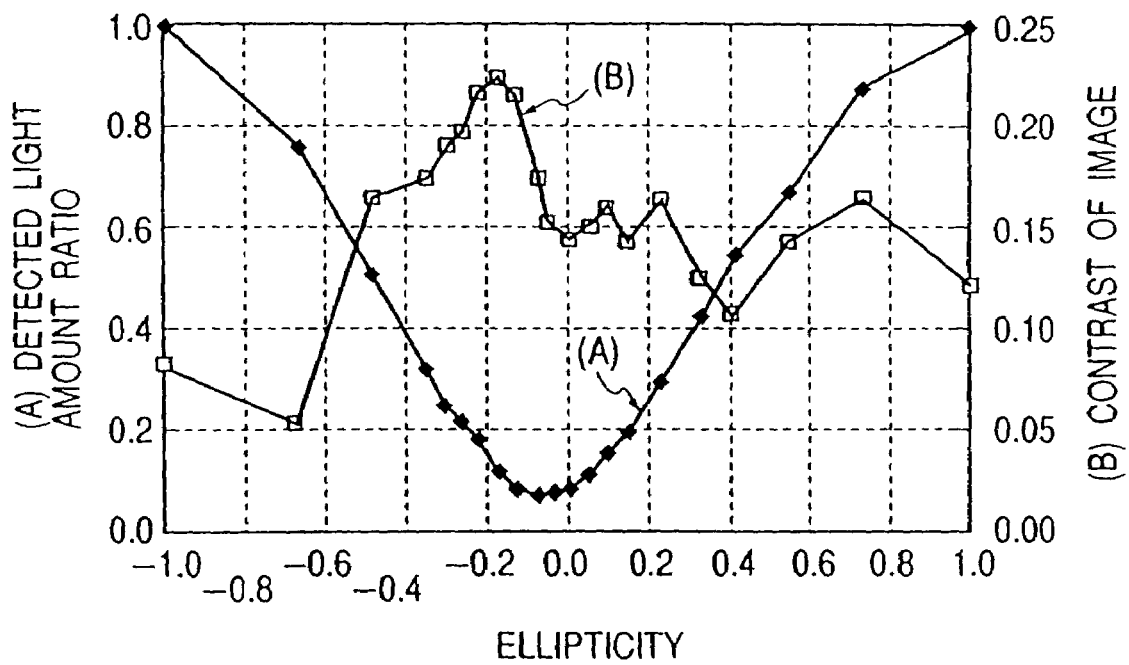
FIG. 11 is a chart showing the relationship between ellipticity and detected light ratio or contrast.

By rotating the ¼ wavelength plate 17, the ellipticity of the elliptically polarized light which illuminates the sample 1 is changed. The relation between an ellipticity and image contrast of the sample 1 detected by the image sensor 70 is illustrated in FIG. 11. The ellipticity is for distinguishing the polarizing direction, clockwise or counterclockwise. The contrast of the image is determined from an image of periodically repeating line patterns formed on the surface of the sample 1. When the light intensity is constant, the amount of light detected by the image sensor 70 decreases with the reduction of the absolute number of the ellipticity. A light intensity ratio is defined as a relative amount of light compared to the circularly polarized light (its ellipticity is 1 or −1).

In FIG. 11, when the ellipticity is −0.18, the contrast is maximized. Therefore, to detect a defect of periodically repeated line patterns, it is desirable to set the ellipticity of the illumination light at approximately −0.18. On the other hand, the light intensity ratio decreases to 0.1 at that ellipticity. So, when detecting a defect by setting the ellipticity of the illumination at approximately −0.18, the intensity of light emitted from the light source 8 needs to be about ten times more than that of when the ellipticity is 1 or −1, a circularly polarized illumination light.

In some cases, ellipticity of the illumination light source to have maximum inspection sensitivity is not the same to that which has a maximum contrast. It is desirable to determine the ellipticity of light as follows. At first, detecting a defect several times by setting the ellipticities of the illuminating light between −0.4 and −0.1, where the contrast of image is relatively high. Then, from the result of the detection, determining the ellipticity of light to obtain a maximum defect detecting sensitivity.

The technique for realizing a high resolution can also apply to a projection type exposure unit to be employed for patterning semiconductors, etc. More specifically, a polarization element is disposed between reticle and wafer so that a polarized light illuminates the reticle, which is an original sheet, and the amplitude of the 0-order diffracted light passing through the reticle becomes equal to the amplitude of a higher-order diffracted light, forming a high contrast reticle image on a wafer coated with a resist. The margin of the resist development is thus increased and thereby improving productivity.

As described above, according to the present invention, it is possible to provide an optical system, which can control the angle between the polarization direction of the electrical field vector and the orientation of the object pattern on the polarizing plane of illumination according to the object pattern formed on the sample, thereby providing high resolution images of defects so as to detect more fine defects. The present invention also makes it possible to set a polarization direction of the electrical field vector on the polarizing plane, light wavelength, etc., more efficiently, thereby providing a higher resolution optical system and a defect inspecting apparatus with a high sensitivity using such a high resolution optical system.

The preceding has been a description of the preferred embodiment of the invention. It will be appreciated that deviations and modifications can be made without departing from the scope of the invention, which is defined by the appended claims.

What is claimed is:

1. A method for observing a sample with patterns formed thereon, including the steps for:
    applying a polarized light to the sample from an optical system set on a first polarizing condition;
    detecting the light applied to and reflected from the surface of the sample through a phase difference plate and an analyzer, thereby obtaining a first image;
    displaying the first image on a monitor screen;
    setting the optical system on a second polarizing condition according to the first image displayed on the monitor screen;
    applying a polarized light to the sample from the optical system set on the second polarizing condition; and
    detecting the light applied to and reflected from the surface of the sample through the phase difference plate and the analyzer, to thereby obtain a second image,
    wherein the phase difference plat is adjusted when the optical system is set in the second polarizing condition, thereby reducing the amplitude of the 0 order diffracted light from a pattern formed on the surface of the sample more than the amplitude of the higher-order diffracted light, both of the 0 order and higher-order diffracted light being included in the light reflected from the surface of the sample.

2. A method for inspecting defects of a sample with patterns formed thereon, the method including steps for:
- applying polarized light to the sample through an objective lens;
- detecting the polarized light applied to and reflected from the surface of the sample through the objective lens, a phase difference plate and an analyzer, thereby obtaining an image of the sample; and
- comparing the obtained image with a corresponding image previously stored, thereby detecting the defects of the sample,
- wherein the phase difference plate reduces the amplitude of the 0 order diffracted light from a pattern formed on the surface of the sample more than the amplitude of the higher-order diffracted light, both of the 0 order and higher-order diffracted lights being included in the light applied to and reflected from the surface of the sample.

3. A method for inspecting defects of a sample in accordance with claim 2 wherein the method further includes a step for displaying the image of the sample formed with the detected light on a monitor screen.

4. The method of claim 2 further comprising generating light and filtering the light to produce filtered light having a limited wavelength, wherein the polarized light is produced from the filtered light.

5. A method for inspecting defects of a sample with patterns formed thereon, including the steps for:
- applying a polarized light to the sample from an optical system set on a first polarizing condition;
- detecting the light applied to and reflected from the sample, to thereby obtain a first image;
- displaying the first image on a monitor screen;
- setting the optical system in a second polarizing condition according to the first image displayed on the monitor screen;
- applying the polarized light to the sample while the optical system is set in the second polarizing condition;
- detecting the light applied to and reflected from the sample, thereby obtaining a second image; and
- comparing the obtained second image with a corresponding image previously stored, thereby detecting defects of the sample,
- wherein the method reduces the amplitude of the 0 order diffracted light from a pattern formed on the surface of the sample more than the amplitude of the higher-order diffracted light when the optical system is set in the second polarizing status, both of the 0 order and higher-order diffracted light being included in the light applied to and reflected from the surface of the sample.

6. An apparatus for inspecting defects of a sample with patterns formed thereon including:
- lighting means for applying a polarized light to the sample through an objective lens;
- polarized light image detecting means for detecting the light reflected from the surface of the sample through an objective lens, a phase difference plate and an analyzer when the polarized light is applied to the sample from the lighting means, thereby obtaining the image of the sample; and
- defect detecting means for comparing the image obtained by the image detecting means with a corresponding image stored beforehand, thereby detecting defects of the sample,
- wherein the phase difference plate has a ½ wavelength plate and a ¼ wavelength plate and is used to reduce the amplitude of the 0 order diffracted light from a pattern formed on the surface of the sample more than the amplitude of the higher-order diffracted light, both of the 0 order and higher-order diffracted lights being included in the light applied to and reflected from the surface of the sample.

7. An apparatus for inspecting defects of a sample in accordance with claim 6 wherein the apparatus is further provided with display means for displaying the image of the sample obtained by the polarized light imaging means on a monitor screen.

8. The apparatus of claim 6 wherein the lighting means comprises a wavelength selecting filter and a polarizer along an optical path of the wavelength selecting filter, the wavelength selecting filter disposed to receive light from a light source and to produce filtered light, wherein the filtered light is received by the polarizer to produce the polarized light.

* * * * *